United States Patent
Liu et al.

(10) Patent No.: US 12,329,837 B2
(45) Date of Patent: Jun. 17, 2025

(54) AQUEOUS SURFACTANT COMPOSITIONS AND SOAP BARS

(71) Applicant: BASF SE, Ludwigshafen (DE)

(72) Inventors: Zhao Ting Liu, Shanghai (CN); Yang Zhang, Shanghai (CN); Ming Hao Gu, Shanghai (CN); Claudia Brunn, Düsseldorf-Holthausen (DE)

(73) Assignee: BASF SE, Ludwigshafen (DE)

( * ) Notice: Subject to any disclaimer, the term of this patent is extended or adjusted under 35 U.S.C. 154(b) by 881 days.

(21) Appl. No.: 17/604,861

(22) PCT Filed: Apr. 27, 2020

(86) PCT No.: PCT/EP2020/061606
§ 371 (c)(1),
(2) Date: Oct. 19, 2021

(87) PCT Pub. No.: WO2020/225005
PCT Pub. Date: Nov. 12, 2020

(65) Prior Publication Data
US 2022/0257486 A1    Aug. 18, 2022

(30) Foreign Application Priority Data

May 7, 2019  (WO) ............... PCT/CN2019/085840
Jun. 7, 2019  (EP) .................................. 19178906

(51) Int. Cl.
*A61K 8/00*   (2006.01)
*A61K 8/02*   (2006.01)
(Continued)

(52) U.S. Cl.
CPC ............ *A61K 8/466* (2013.01); *A61K 8/0216* (2013.01); *A61K 8/732* (2013.01); *A61K 8/738* (2013.01);
(Continued)

(58) Field of Classification Search
CPC ..................................................... A61K 8/466
See application file for complete search history.

(56) References Cited

U.S. PATENT DOCUMENTS 2,894,912 A   7/1959  Geitz
3,297,579 A   1/1967  Weil et al.
(Continued)

FOREIGN PATENT DOCUMENTS

AR   099237 A1   7/2016
AR   099238      7/2016
(Continued)

OTHER PUBLICATIONS

International Preliminary Report on Patentability received for PCT Patent Application No. PCT/EP2020/061606, mailed on Nov. 18, 2021, 9 pages.
(Continued)

*Primary Examiner* — Necholus Ogden, Jr.
(74) *Attorney, Agent, or Firm* — Faegre Drinker Biddle & Reath LLP

(57) ABSTRACT

Suggested are surfactant compositions comprising: One or more alpha-sulfofatty acid disalts (A) of general formula (I), RICH (SO3M1) COOM2 (I), wherein the radical R 1 denotes a linear or branched alkyl or alkenyl radical having 6 to 18 C atoms and the radicals M 1 and M 2-independently of one another-are selected from the group H, Li, Na, K, Ca/2, Mg/2, Ammonium and alkanolamines and one or more polysaccharides (B) selected from the group consisting of dextrin and its derivatives, starch and its derivatives, cellulose and its derivatives, preferably one or more dextrins (B) of the general formula (II), (II) in which n is an integer between 3 and 200.

(Continued)

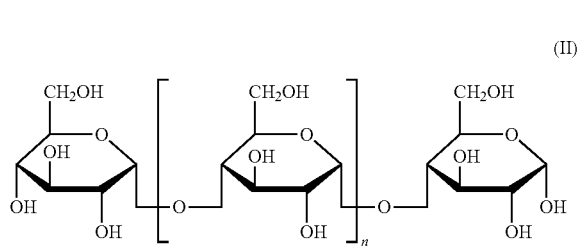

(II)

10 Claims, 2 Drawing Sheets

Figure 1:
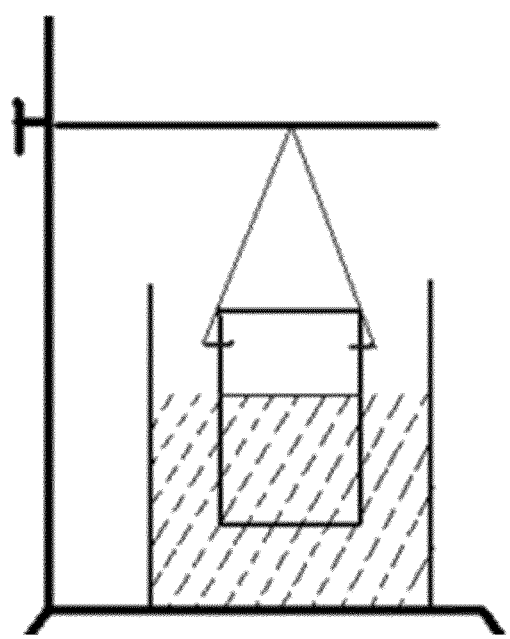

(51) Int. Cl.
    *A61K 8/46*     (2006.01)
    *A61K 8/73*     (2006.01)
    *A61Q 5/02*     (2006.01)
    *C11D 1/28*     (2006.01)
    *C11D 3/22*     (2006.01)
    *C11D 17/00*     (2006.01)

(52) U.S. Cl.
    CPC .................. *A61Q 5/02* (2013.01); *C11D 1/28* (2013.01); *C11D 3/222* (2013.01); *C11D 17/0065* (2013.01)

(56) References Cited

U.S. PATENT DOCUMENTS

| | | |
|---|---|---|
| 4,100,097 A | 7/1978 | O'Roark |
| 4,861,508 A | 8/1989 | Wegener et al. |
| 5,200,115 A | 4/1993 | Giesen et al. |
| 6,846,786 B1 | 1/2005 | Patel et al. |
| 10,370,618 B2 | 8/2019 | Behler et al. |
| 10,736,832 B2 | 8/2020 | Max et al. |
| 10,792,237 B2 | 10/2020 | Brunn et al. |
| 2012/0208898 A1 | 8/2012 | Dong et al. |
| 2013/0034515 A1 | 2/2013 | Stone et al. |
| 2014/0053508 A1 | 2/2014 | Chourey et al. |
| 2017/0007520 A1 | 1/2017 | Brunn et al. |
| 2017/0172892 A1* | 6/2017 | Dai .................. C11D 3/2093 |
| 2019/0254946 A1 | 8/2019 | Brunn et al. |

FOREIGN PATENT DOCUMENTS

| | | |
|---|---|---|
| AR | 101690 | 1/2017 |
| CN | 1040389 A | 3/1990 |
| JP | 08-073891 A | 3/1996 |
| JP | 09-059134 A | 3/1997 |
| JP | 2004-035563 A | 2/2004 |
| JP | 2007-508403 A | 4/2007 |
| JP | 2014-513163 A | 5/2014 |
| JP | 2017-505813 A | 2/2017 |
| JP | 2019-523771 A | 8/2019 |
| WO | WO-92/07931 A1 | 5/1992 |
| WO | WO-03/063819 A1 | 8/2003 |
| WO | WO-2006/062665 A1 | 6/2006 |
| WO | WO-2007/133582 A1 | 11/2007 |

OTHER PUBLICATIONS

"Seibella Moisturizing Shampoo", Melaleuca (China) Daily Necessities Co., Ltd., Product packaging plan, Apr. 7, 2016, 1 page.
International Application No. PCT/EP2020/061606, International Search Report and Written Opinion, mailed Jul. 23, 2020.
European Search Report for EP Patent Application No. 19178906.4, Issued on Nov. 13, 2019, 3 pages.

* cited by examiner

AQUEOUS SURFACTANT COMPOSITIONS AND SOAP BARS

CROSS-REFERENCE TO RELATED APPLICATIONS

This is the U.S. national phase of International Application No. PCT/EP2020/061606, filed Apr. 27, 2020, which claims the benefit of International Application No. PCT/CN2019/085840, filed May 7, 2019, and European Patent Application No. 19178906.4, filed Jun. 7, 2019.

FIELD OF THE INVENTION

The present invention relates to surfactant compositions especially aqueous surfactant compositions and solid surfactant compositions with a content of alpha-sulfo fatty acid disalts and polysaccharides.

PRIOR ART

Anionic surfactants are some of the most widespread interface-active compounds and, apart from being used in detergents and cleaners, are also used for diverse purposes in the field of cosmetics. Customary anionic surfactants as are used in particular in cosmetics are the salts of alkyl ether sulfates (alkyl polyether sulfates, fatty alcohol polyglycol ether sulfates, in short also ether sulfates). They are characterized by a strong foaming ability, high cleaning power, low sensitivity to hardness and grease and are used widely for producing cosmetic products such as, for example, hair shampoos, foam or shower baths, but also in hand dishwashing detergents.

For many current applications, apart from a good interface-active effect, further requirements are placed on anionic surfactants. A high dermatological compatibility is required in particular in cosmetics. Furthermore, an adequate solubility in water, good compatibility with as many as possible of the active ingredients and auxiliaries used in cosmetics, a good foaming ability and good thickenability are generally desired. Especially for hair care compositions the dermatological compatibility and ease of use are objects of new developments.

Furthermore, there is a need for anionic surfactants which can be produced at least partially from biogenic sources and specifically also renewable raw materials. In addition, there is also a need for surfactants which have no alkoxylated groups and which thus render superfluous in particular the use of ethylene oxide for their production.

US application US 2012/208898 discloses aqueous personal care compositions comprising salts of sulfonated fatty acid esters and/or salts of sulfonated fatty acids in combination with alkyl betaines as hair care formulations. Salts of sulfonated fatty acid esters are well tolerated surfactants, but due to their good water solubility it is difficult to form solid surfactant compositions with these surfactants.

It was an object of the invention to provide a composition for skin cleansing which provides an easy rinse-off feeling and skin smoothness, softness and less skin dryness after rinsing.

Especially for hair treatment it was another object to achieve a conditioning effect without stickiness and long drying time. Improved drying properties of hair-care surfactant compositions for a time-saving use (quick-dry effect on hair) are an important object.

Anionic surfactants are very often used surfactants in solid compositions. In former times solid cleaning bars which were conventional soap bars contained alkali metal salts of fatty acids (soaps in the classical sense), but in recent years cleaning bars were also made from surfactants. Soap-like bars consisting entirely of synthetic detergent compositions were called syndet bars, the combination of salts of fatty acids with surfactants was marketed as combibars. Conventional soaps being salts of fatty acids provide an alkaline environment due to hydrolysis in aqueous solution at a pH of 10.2-10.4, which is resulting in a damage of the epidermis, the natural protection of the skin which normally has an acid pH of approximately 5.5-6.5. Destroying the natural skin barrier by permanent use of these surfactant soaps leads to a bad skin tolerance with itching, dehydration and cracking of the epidermis. In order to overcome these disadvantages "re-fatting agents" such as fatty and oily ingredients selected from natural oils, mineral oil, petrolatum, stearic acid or lanolin, or "moisturizers" for example glycerin, urea and sorbitol have been incorporated into soap bars, these re-fatting agents often result in a sticky feeling and increase the drying time. Furthermore, the addition of these additives entails the drawback of poor foaming and cleaning properties of the soaps. In addition conventional soaps have undesirable scum- or curd-forming characteristics due to their incompatibility with hard water and bad solubility of their calcium salts.

The same partly applies to common fillers of soaps which are used to reduce the costs and improve the handling of the bars by providing a sufficient firmness. Years ago sodium silicate, talc or borax have been used as main components. However, these fillers are not very well tolerated especially for sensitive skin. In the International Patent Application WO 92/07931 surfactant bars of common anionic surfactants and polysaccharides are disclosed. Talc, clay, calcium carbonate and dextrin are listed as possible filler materials.

Preferred surfactants used in syndet bars were alkali metal salts of acyl isethionates, fatty alcohol sulfates or alkane sulfonates which are still the predominantly used surfactants in surfactant containing bars.

U.S. Pat. No. 2,894,912 discloses a detergent bar consisting of an alkali metal salt of esters of isethionic acid; mixed aliphatic acids; a so-called suds-boosting detergent salt, e.g., alkyl aryl sulfonates; water; a higher fatty acid soap; and a higher fatty acid.

U.S. Pat. No. 4,100,097 is related to a synthetic detergent bar which consists of coconut-oil fatty acid ester of sodium isethionate and/or sodium lauryl sulfoacetate, paraffin, powdered starch, dextrin, coconut-oil fatty acid and water.

The necessary quantities of synthetic detergents in surfactant bars often result in mushiness and poor firmness, tackiness, difficulties in manufacturing, cracking of the bars and poor foaming properties. Furthermore, the use of these surfactants is currently decreased for environmental reasons and substitutes free of impurities of ethylene oxide and sulfates which are made of raw materials from renewable resources are more and more in favor.

The patent family related to the International Patent Applications WO 03/063819, WO 06/062665 and WO07/133582 is disclosing the combination of C6 to C22-fatty acid salts, a polyhydric alcohol and a mixture of anionic surfactants comprising alpha sulfonated alkyl ester and a sulfonated fatty acid. These compositions show improved processability and improved after-feel properties to the skin. However, the high amount of at least 40 wt % of a fatty acid soap still results in the disadvantages of the conventional soap of fatty acid salts and it was a major object to avoid a high amount of conventional soaps.

From the above, it is apparent that there is still a need for solid surfactant compositions made of well tolerable detergents which have a pH approximating that of a person's skin and anyhow show good handling, foaming and cleaning properties. The processing of solid surfactant compositions should easily be possible. Hence it was another object to provide the anionic surfactant in form of a solid surfactant containing composition with good foaming properties, surfactant mildness, a good compatibility with water hardness and increased firmness.

Hair treatment with the surfactant composition should as well be possible in form of solid surfactant compositions, these should show an advanced foaming behavior during rinsing, a conditioning effect and an improved drying time compared to a commercially available surfactant compositions, e.g. surfactant bars with Sodium Cocoyl Isethionate.

DESCRIPTION OF THE INVENTION

The object of the present invention was to provide improved surfactant compositions with a content of well-tolerable anionic surfactants which are liquid aqueous surfactant compositions or solid compositions.

This object was solved by a surfactant composition comprising
one or more alpha-sulfo fatty acid disalts (A) of the general formula (I),

$$R^1CH(SO_3M^1)COOM^2 \qquad (I)$$

in which the radical $R^1$ is a linear or branched alkyl or alkenyl radical with 6 to 16 carbon atoms and the radicals $M^1$ and $M^2$—independently of one another—are selected from the group H, Li, Na, K, Ca/2, Mg/2, ammonium and alkanolamine,
one or more polysaccharides (B) selected from the group consisting of dextrin and its derivatives, starch and its derivatives and cellulose and its derivatives, where the following provisos apply:
if the surfactant composition comprises one or more ester sulfonates (E) of the general formula (V),

$$R^2CH(SO_3M^7)COOR^3 \qquad (V)$$

in which the radical $R^2$ is a linear or branched alkyl or alkenyl radical with 6 to 18 carbon atoms and the radical $R^3$ is a linear or branched alkyl or alkenyl radical with 1 to 20 carbon atoms, where the radical $R^3$ can logically be an alkenyl radical or be branched only above 3 carbon atoms, and the radical $M^7$ is selected from the group Li, Na, K, Ca/2, Mg/2, ammonium and alkanolamines, it is the case that the compounds (A)—based on the sum of the compounds (A) and (E)—must be present to more than 50% by weight.

The surfactant compositions are characterized by an excellent foaming ability, in particular initial foaming behavior. The initial foaming behavior plays a very important role for so-called rinse-off products, which are to be understood as meaning products which come into contact with the skin or hair during cleaning or grooming, but are then washed off again (e.g. shower gels, shower formulations, shampoos, liquid soaps, etc.). In this sector, as large a foam volume as possible is desired.

The surfactant compositions moreover have a hydrolysis stability both in the acidic and in the alkaline pH range and avoid constituents which comprise ethylene or propylene oxide building blocks for ecological reasons as well as surfactants with sulfate groups to improve skin and mucosa tolerability.

The surfactant compositions also have a storage stability at room temperature (23° C.) of more than at least 8 weeks without any kind of visible changes (for example clouding, phase separations, discoloration and the like) occurring and without viscosity changes or changes in the chemical composition arising.

The inventive surfactant compositions are aqueous surfactant compositions, which are liquid aqueous surfactant compositions or solid compositions.

The amount of water in the solid composition is 1% to 20 wt %, preferably 5 to 15 wt %, more preferably 7 to 15 wt %. The amount of water in the liquid aqueous compositions is more than 30 wt %, preferably more than 40 wt % more preferably more than 50 wt % based on the aqueous composition.

Due to the low skin tolerability it is an object to reduce the amount of anionic surfactants in personal care and household products. The surfactant compositions of the current invention should comprise less than 40% by weight, preferably less than 25% by weight, most preferably less than 15% by weight anionic surfactants other than compounds (A) and (C) based on the weight of the composition. Very often other anionic surfactants are conventional soaps, which are alkali salts of fatty acids. In case of solid compositions the fatty acid is mainly a saturated C12 to C22 fatty acid, especially stearic acid. Compositions comprising salts of long chain fatty acids, especially stearic acid are difficult to handle because of their incompatibility with water hardness, poor foaming properties, scum- or curd-forming characteristics and low skin tolerability resulting from the alkaline pH-value. Therefore the compositions of the current invention should comprise less than 30% by weight, preferably less than 20% by weight, most preferably less than 10% by weight of fatty acid salts of stearic acid based on the weight of the composition.

Preferably the invention provides surfactant compositions comprising
one or more alpha-sulfo fatty acid disalts (A) of the general formula (I),

$$R^1CH(SO_3M^1)COOM^2 \qquad (I)$$

in which the radical $R^1$ is a linear or branched alkyl or alkenyl radical with 6 to 16 carbon atoms and the radicals $M^1$ and $M^2$—independently of one another—are selected from the group H, Li, Na, K, Ca/2, Mg/2, ammonium and alkanolamine,
one or more dextrins (B) of the general formula (II),

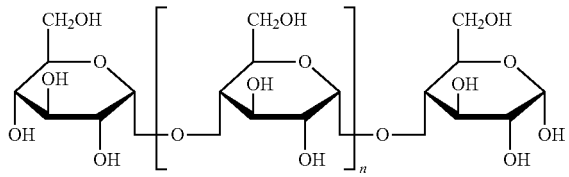

in which n—the average degree of polymerization—is an integer between 3 and 200, preferably between 5 and 100, and most preferably between 10 and 40.
where the following provisos apply:
if the aqueous surfactant compositions comprise one or more ester sulfonates (E) of the general formula (V),

$$R^3CH(SO_3M^5)COOR^4 \qquad (V)$$

in which the radical $R^3$ is a linear or branched alkyl or alkenyl radical with 6 to 18 carbon atoms and the radical $R^4$ is a linear or branched alkyl or alkenyl radical with 1 to 20 carbon atoms, where the radical $R^4$ can logically be an alkenyl radical or be branched only above 3 carbon atoms, and the radical $M^5$ is selected from the group Li, Na, K, Ca/2, Mg/2, ammonium and alkanolamines, it is the case that the compounds (A)—based on the sum of the compounds (A) and (E)—must be present to more than 50% by weight, preferably more than 60% by weight, more preferably more than 70% by weight and most preferably more than 95% by weight.

Solid compositions comprising anionic surfactants with good foaming properties should have improved characteristics in anti-mush performance and faster drying performance in order to be suitable for treating hair, preferable as hair care compositions for shampooing. Surprisingly solid compositions comprising alpha-sulfo fatty acid disalts and polysaccharides selected from the group consisting of dextrin and its derivatives, starch and its derivatives and cellulose and its derivatives show improved anti-mush performance and have a fast drying performance after hair treatment.

"A composition suitable for treating hair" according to the present invention can be any composition suitable for cleansing hair, it can be a composition for conditioning hair (a conditioner), it can be a mask for treating hair. The solid surfactant composition could be a combination bar or a syndet bar.

Preferably the invention provides solid surfactant compositions comprising
one or more alpha-sulfo fatty acid disalts (A) of the general formula (I),

$$R^1CH(SO_3M^1)COOM^2 \qquad (I)$$

in which the radical $R^1$ is a linear or branched alkyl or alkenyl radical with 6 to 16 carbon atoms and the radicals $M^1$ and $M^2$—independently of one another—are selected from the group H, Li, Na, K, Ca/2, Mg/2, ammonium and alkanolamine,
one or more polysaccharides (B) selected from the group consisting of dextrin and its derivatives, starch and its derivatives, cellulose and its derivatives,
where the following provisos apply:
if the surfactant composition comprises one or more ester sulfonates (E) of the general formula (V),

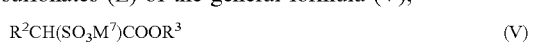
$$R^2CH(SO_3M^7)COOR^3 \qquad (V)$$

in which the radical $R^2$ is a linear or branched alkyl or alkenyl radical with 6 to 18 carbon atoms and the radical $R^3$ is a linear or branched alkyl or alkenyl radical with 1 to 20 carbon atoms, where the radical $R^3$ can logically be an alkenyl radical or be branched only above 3 carbon atoms, and the radical $M^7$ is selected from the group Li, Na, K, Ca/2, Mg/2, ammonium and alkanolamines, it is the case that the compounds (A)—based on the sum of the compounds (A) and (E)—must be present to more than 50% by weight, preferably more than 60% by weight, more preferably more than 70% by weight and most preferably more than 95% by weight.

More preferably the invention provides solid surfactant compositions comprising
one or more alpha-sulfo fatty acid disalts (A) of the general formula (I),

$$R^1CH(SO_3M^1)COOM^2 \qquad (I)$$

in which the radical $R^1$ is a linear or branched alkyl or alkenyl radical with 6 to 16 carbon atoms and the radicals $M^1$ and $M^2$—independently of one another—are selected from the group H, Li, Na, K, Ca/2, Mg/2, ammonium and alkanolamine,
one or more dextrins (B) of the general formula (II),

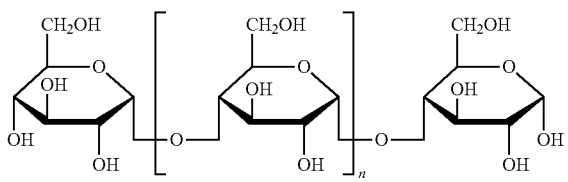

in which n—the average degree of polymerization—is an integer between 3 and 200, preferably between 5 and 100, and most preferably between 10 and 40, where the following provisos apply:
if the surfactant composition comprises one or more ester sulfonates (E) of the general formula (V),

$$R^3CH(SO_3M^5)COOR^4 \qquad (V)$$

in which the radical $R^3$ is a linear or branched alkyl or alkenyl radical with 6 to 18 carbon atoms and the radical $R^4$ is a linear or branched alkyl or alkenyl radical with 1 to 20 carbon atoms, where the radical $R^4$ can logically be an alkenyl radical or be branched only above 3 carbon atoms, and the radical $M^5$ is selected from the group Li, Na, K, Ca/2, Mg/2, ammonium and alkanolamines, it is the case that the compounds (A)—based on the sum of the compounds (A) and (E)—must be present to more than 50% by weight, preferably more than 60% by weight, more preferably more than 70% by weight and most preferably more than 95% by weight.

The amount of water in the solid composition is 1% to 20 wt %, preferably 5 to 15 wt %, more preferably 7 to 15 wt % based on the weight of the composition. Preferably the solid composition comprises less than 30% by weight, preferably less than 20% by weight, most preferably less than 10% by weight of fatty acid salts of stearic acid based on the weight of the composition.

The Compounds (A)

The compounds (A), which are referred to within the context of the present invention as alpha-sulfo fatty acid disalts, are obligatory for the aqueous and solid surfactant compositions according to the invention. They have the afore mentioned formula (I)

$$R^1CH(SO_3M^1)COOM^2 \qquad (I)$$

in which the radical $R^1$ is a linear or branched alkyl or alkenyl radical with 6 to 16 carbon atoms and the radicals $M^1$ and $M^2$—independently of one another—are selected from the group H, Li, Na, K, Ca/2, Mg/2, ammonium and alkanolamines. Particularly preferred alkanolamines of the invention are Monoethanolamine, Diethanolamine, Triethanolamine and Mono-Isopropanolamine.

In the context of the present invention the compounds (A) named as "alpha-sulfo fatty acid disalts" are defined by formula (I) in which the radicals $M^1$ and $M^2$—independently of one another—are selected from the group H, Li, Na, K, Ca/2, Mg/2, ammonium and alkanolamines and thus encompass a disalt and/or a monosalt and/or a protonated acid.

In one embodiment, the proviso applies that the fraction of the compounds (A) in the surfactant compositions in which the radical $R^1$ is an alkenyl radical—based on the total amount of the compounds (A)—is 3% by weight or less.

In a preferred embodiment, the radical $R^1$ in the formula (I) means a saturated, linear radical with 10 to 16 carbon atoms, where, with regard to the compounds (A), it is the case that the fraction of the compounds (A) in which the radical $R^1$ is a decyl and/or a dodecyl radical—based on the total amount of the compounds (A)—is more than 70% by weight, preferably more than 80% by weight, more preferably more than 90% by weight and particular more than 95% by weight .

Preferably, the radicals $M^1$ and $M^2$ in the formula (I) are Na.

The liquid aqueous compositions usually comprise more than 0.1 to 10% by weight of alpha-sulfo fatty acid disalts (A), preferably more than 1 to 8%, more preferably 3 to 6% by weight of alpha-sulfo fatty acid disalts based on the weight of the composition. The solid compositions usually comprise 10 to 90% by weight of alpha-sulfo fatty acid disalts (A), preferably 20 to 70%, more preferably 30 to 50% by weight of alpha-sulfo fatty acid disalts based on the weight of the composition.

The compounds (A) can be prepared by all methods known appropriately to the person skilled in the art. A particularly preferred method of preparation here is the sulfation of the corresponding carboxylic acids. Here, the corresponding carboxylic acid and in particular the corresponding fatty acids are reacted with gaseous sulfur trioxide, the sulfur trioxide being used preferably in an amount such that the molar ratio of $SO_3$ to fatty acid is in the range from 1.0:1 to 1.1:1. The crude products obtained in this way, which are acidic sulfonation products, are then partially or completely neutralized, preference being given to complete neutralization with aqueous NaOH. If desired, it is also possible to undertake purification steps and/or a bleaching (for adjusting the desired pale color of the products).

In a particularly preferred embodiment, the compounds (A) are used in technical-grade form. This means that the corresponding carboxylic acids, in particular native fatty acid, are sulfonated with gaseous sulfur trioxide, as a result of which, following partial or complete neutralization of the resulting acidic sulfonation products, a mixture of the compounds (A), (C) and (D) results. By virtue of corresponding adjustments of the reaction parameters (in particular molar ratio of carboxylic acid and sulfur trioxide, and also reaction temperature) it is possible to control the ratio of the compounds (A), (C) and (D). The compounds (C) and (D) are described below in the chapter "Preferred embodiments".

Within the context of the present invention, preference is given to those technical-grade mixtures of the alpha-sulfo fatty acid disalts which have the following composition:
the content of (A) is in the range from 60 to 100% by weight, preferably in the range from 70 to 85% by weight,
the content of (C) is in the range from 0 to 20% by weight, preferably in the range from 5 to 15% by weight,
the content of (D) is in the range from 0 to 20% by weight, preferably in the range from 10 to 15% by weight,
with the proviso that the sum of the components (A), (C) and (D) in this mixture is 100% by weight.
The Compounds (B)

The function of compound (B) in the aqueous surfactant composition is based on its conditioning and hair care effects for liquid and solid compositions and its filling and forming properties for solid compositions.

The liquid aqueous compositions usually comprise 0.1 to 10% by weight of polysaccharides, preferably 0.2 to 5%, more preferably 1 to 3% by weight of polysaccharides based on the weight of the composition.

The solid compositions usually comprise 1 to 60% by weight of polysaccharides, preferably 5 to 50%, more preferably 15 to 40% by weight of polysaccharides based on the weight of the composition.

For the solid surfactant compositions the compounds B are fillers. The function of the filler is to enable the use of the surfactants in a solid form, to fortify the composition, to increase the wear rate, firmness and sensory feeling of the composition while decreasing the cost while not compromising foaming performance of the anionic surfactant.

Preferred fillers for solid surfactant compositions are polysaccharide powder such as dextrin and its derivatives, starch and its derivatives, cellulose and its derivatives.

The compounds (B), which are referred to in the context of the present invention as polysaccharides are selected from the group consisting of dextrin and its derivatives, starch and its derivatives, cellulose and its derivatives, at least one of these is obligatory for the surfactant compositions according to the invention.
Starch and its Derivatives
Starch The binder/filler component could be an untreated starch or a modified powdered hydrolyzed starch or a derivative. In solid compositions this should be present in an amount ranging from about 5% up to about 20% by weight and preferably in an amount ranging from about 7% to about 12% by weight.

Starch derivatives used in food production and cosmetics such as oxidized starch, monostarch phosphate, distarch phosphate, phosphated distarch phosphate, acetylated distarch phosphate, acetylated starch, acetylated distarch adipate, hydroxypropylstarch, hydroxypropyldistarch phosphate are possible fillers and binders as well. It is particularly preferred to use unsubstituted potato, wheat and/or corn starch which may be used in untreated form or preferably in digested, i.e. partly hydrolyzed, form.
Cellulose and its Derivatives In food industry and cosmetic products cellulose ethers are often used as thickeners, besides this function they are as well used as fillers and binders.

Suitable cellulose derivatives are, for example, cellulose ethers. Cellulose ethers are manufactured by substitution of hydrogen atoms on the hydroxyl groups of the cellulose by alkyl groups and/or arylalkyl groups, these alkyl and/or arylalkyl groups could further be substituted by nonionic, anionic, cationic or nonionic groups. The alkyl groups are typically linear or branched C1-C8 alkyl groups. The preferred alkyl group is a C1-C4 alkyl group, examples being methyl, ethyl, n-propyl, isopropyl, n-butyl, sec-butyl, isobutyl or tert-butyl. The alkyl group may be substituted by an aromatic radical to form the arylalkyl group, such as with a phenyl radical, for example. One preferred arylalkyl group is benzyl. The alkyl or arylalkyl group may be functionally substituted, by hydroxyl, carboxyl or carboxylate groups, for example. Where carboxylate groups are present, corresponding counterions are present as well, examples being alkali metal ions such as sodium or potassium, or ammonium ions. It is also possible to use mixed cellulose ethers, which contain more than one kind of alkyl, arylalkyl or functionally substituted alkyl groups.

Preferred hydrophilic polymeric cellulose derivatives are methyl-, ethyl-, propyl-, carboxymethyl-, hydroxyethyl-, hydroxypropyl-, hydroxypropylmethyl-, ethylmethylcellulose-, methylhydroxyethyl-, methylhydroxybutyl-, ethylhydroxyethyl- and /or carboxymethylhydroxyethylcellulose. Among the carboxymethylcelluloses, sodium carboxymethylcellulose, crosslinked sodium carboxymethyl-cellulose or enzymatically hydrolyzed carboxymethylcellulose.

Dextrins and its Derivatives

Dextrins and its derivatives include dextrins, maltodextrins and cyclodextrins. The most preferred compounds (B), in the context of the present invention are dextrins. They have the afore mentioned formula (II),

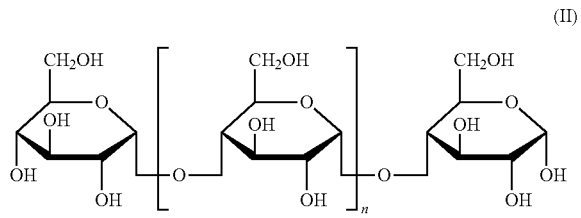

(II)

in which n—the average degree of polymerization—is an integer between 3 and 200, preferably between 5 and 100, and most preferably between 10 and 40.

Dextrins are a group of low molecular weight carbohydrates obtainable by the hydrolysis of starch forming D-glucose units linked by $\alpha$-(1→4) bonding starting with an $\alpha$-(1→6) glycosidic bond.

Preferably they have a dextrose equivalent between 1 and 30%, preferably between 1 and 13% based on dextrose (glucose) with 100%. Dextrose equivalent (DE) is a measure of the amount of reducing sugars present in a sugar product, expressed as a percentage on a dry basis relative to dextrose. The dextrose equivalent gives an indication of the average degree of polymerisation (DP) for starch sugars, it is inversely related to the molecular weight. The degree of polymerization (DP) is an indicator of the degree of hydrolysis, unhydrolysed starch has a DE of 0 while glucose has a DE value of 100.

These polysaccharides are produced from starch using enzymes like amylases or by dry heating under acidic conditions (pyrolysis or roasting). Industrial production of dextrins is generally performed by acidic hydrolysis of potato starch. Finished dextrins are a very fine powder in various colors from pure white to brown. Depending on their molecular weight and color three main types of dextrins are differentiated: white dextrins, canary or yellow dextrins, and Britisch gums. British gums are dextrins with the highest molecular weight with an average degree of polymerization of about 20 and strong adhesive properties, yellow dextrins are the lowest in molecular weight, while the white dextrins have a molecular weight between the other types. They are often used in adhesives and coatings which come in contact with food products.

Although not the preferred dextrins, maltodextrins can as well be included as polysaccharides and dextrin derivatives in the composition. They are composed of $\alpha$-(1→4) bonding glucose only and have an average polymerization degree of between 10 and 20 and a dextrose equivalent of 3 to 20%, preferably 10 to 20%.

The cyclodextrin can be any of the known cyclodextrins such as, unsubstituted cyclodextrins containing from six to twelve glucose monomers, especially, alpha-, beta-, and gamma-cyclodextrins, and/or their derivatives, and/or mixtures thereof. The alpha-, beta-, and gamma-cyclodextrins contain 6, 7, and 8 glucose monomer units, respectively, arranged in a donut-shaped ring. Examples of cyclodextrin derivatives suitable for use in the present invention include methyl beta-cyclodextrin, hydroxy-ethyl beta-cyclodextrin, and hydroxypropyl beta-cyclodextrin of different degrees of substitution. Water-soluble cyclodextrin derivatives are preferred cyclodextrin derivatives. Preferably at least a major portion of the cyclodextrins is alpha-, beta- and/or gamma-cyclodextrins, more preferably alpha- and beta-cyclo-dextrins. An especially preferred cyclodextrin for use in the present invention is beta-cyclodextrin. It is also preferred to use mixtures of cyclodextrins.

In the present invention the amount of dextrins is responsible for the improved drying effect, a conditioning effect of aqueous surfactant compositions not compromising foaming performance of the anionic surfactant and for the processability of the solid surfactant compositions.

The liquid aqueous compositions usually comprise 0.1 to 10% by weight of dextrins, preferably 0.2 to 5%, more preferably 1 to 3% by weight of dextrins based on the weight of the composition. It has been shown to improve the hair blow drying speed if used for hair cleansing and depending on its Dextrose equivalent it could improve building up the viscosity of the liquid aqueous compositions.

The solid compositions usually comprise 1 to 60% by weight of dextrins, preferably 5 to 50%, more preferably 15 to 40% and most preferably between 25 and 35% by weight of dextrins based on the weight of the composition. Dextrins allow the processing of solid compositions with alpha-sulfo fatty acid disalts, they enable the shaping of the solids. By using these solid compositions in hair care compositions a good conditioning effect is achieved while improving the hair blow drying speed.

Further Additives

The solid surfactant and liquid aqueous compositions may contain further additives such as skin moisturizers for example sodium lactate, glycerin, pyrrolidone carboxylic acid; pH-regulans, complexing agents; colorants; whiteners; perfumes; salts such as sodium chloride, sodium sulfate, sodium phosphates; antioxidants, antimicrobial agents and preservatives or stabilizers.

The surfactant compositions preferably contain a pH-regulans, the most preferred one is citric acid which is added in an amount of 1 to 10 wt %, preferably 1 to 6 wt % based on the weight of the composition. In order to achieve a good skin tolerability the pH of a 10 wt % solution of the composition in water has a value of 4 to 7, preferably 4.5 to 6.0.

Preferred Embodiments

In one embodiment, the surfactant compositions according to the invention comprise, besides the compounds (A) and (B) additionally one or more compounds (C) of the general formula (III)

(III)

In the formula (III), the radical $R^4$ is a linear or branched alkyl or alkenyl radical with 7 to 19 carbon atoms, preferably $R^4$ is a saturated, linear alkyl radical having 11 to 15 carbon atoms, with respect to the compounds (C) that the proportion of the compounds (C) in which the radical $R^4$ is an undecyl or a tridecyl radical,—based on the total amount of the compounds (C)—is more than 60% by weight.and the radical $M^3$ is selected from the group H, Li, Na, K, Ca/2, Mg/2, ammonium and alkanolamines. Particularly preferred alkanolamines are Monoethanolamine, Diethanolamine, Triethanolamine and Mono-Isopropanolamine.

In one embodiment, the surfactant compositions according to the invention comprise, besides the compounds (A), (B), additionally one or more inorganic salts of sulfuric acid (D) of the general formula (IV)

$$(M^4)_2SO_4 \qquad (IV)$$

where $M^4$ is selected from the group Li, Na, K, Ca/2, Mg/2, ammonium and alkanolamine.

The radicals $M^1$ and $M^2$ of the compounds (A), the radical $M^3$ of the compounds (C) and the radical $M^4$ of the compounds (D) can be alkanolamines. In this connection, particular preference is given to monoethanolamine, diethanolamine, triethanolamine and monoisopropanolamine.

In a preferred embodiment, the surfactant compositions according to the invention comprise the compounds (A), (B), (C) and (D). Here, it is particularly preferred if $M^1$ and $M^2$ of the compounds (A) are selected from the group H(hydrogen) and Na (sodium).

In one embodiment, the surfactant compositions according to the invention comprise, besides the compounds (A), (B) additionally one or more compounds (F) of the formula (VI)

$$R^5CH_2-CO-CHR^6(SO_3M^6) \qquad (VI),$$

wherein the radicals $R^5$ and $R^6$ mean—independently of one another—linear or branched alkyl radical with 6 to 18 carbon atoms and the radical $M^6$ selected from the group H, Li, Na, K, Ca/2, Mg/2, ammonium and alkanolamines. Particularly preferred alkanolamines are monoethanolamine, diethanolamine, triethanolamine and mono-isopropanolamine.

Use of the Compositions

A further subject matter of the invention is the use of the aforementioned compositions for cosmetic products and wash and cleansing products.

With regard to cosmetic products comprising rinse-off and leave on compositions for skincare particular preference is given here especially to those which are present in the form of hair shampoos, solid surfactant compositions, shower gels, soaps, syndets, washing pastes, washing bars, washing lotions, scrub preparations, foam baths, oil baths, shower baths, soap bars, shaving foams, shaving lotions, shaving creams, lotions and creams and dental care products (for example toothpastes, mouthwashes and the like). Preferred cosmetic products are hair care compositions such as shampoos, especially preferred are solid surfactant compositions as syndet bars for cosmetic cleaning and for use as hair care composition.

In particular, low-pH agents are preferred for cleaning hard surfaces, such as bath and toilet cleaners such as rim blocks and the like, as well as cleaning and/or fragrance gels for use in sanitary facilities.

Solid Surfactant Compositions

The solid surfactant compositions are suitable in various forms, such as bars, noodles, beads, granules, pads, needles, sheets or tablets depending on their manufacturing process and intended use.

The preferred solid surfactant composition with a particularly favorable feeling on the skin and a creamy foam according to the invention comprises:
  30 to 70 wt % of alpha-sulfo fatty acid disalts (compound A)
  10 to 50 wt % of dextrins (compound B)
  5 to 20 wt % water
based on the weight of the solid surfactant composition (the wt % are active material of the respective compounds).

More preferred the solid surfactant composition according to the invention comprises:
  30 to 50 wt % of alpha-sulfo fatty acid disalts (compound A)
  20 to 40 wt % of dextrins (compound B)
  10 to 15 wt % water
based on the weight of the solid surfactant composition.

Most preferred the solid surfactant composition according to the invention comprises:
  35 to 45 wt % of alpha-sulfo fatty acid disalts (compound A)
  23 to 35 wt % of dextrins (compound B)
  7 to 15 wt % water
based on the weight of the solid surfactant composition.

Specifically the most preferred solid surfactant compositions according to the invention comprise:
  40 to 44 wt % of alpha-sufo fatty acid disalts (compound A)
  26 to 30 wt % of dextrins (compound B)
  7 to 15 wt % water
based on the weight of the solid surfactant composition.

The solid surfactant compositions comprising alpha-sulfo fatty acid disalts, dextrin and water preferably contain a pH-regulans, the most preferred one is citric acid which is added in an amount of 1 to 10 wt %, preferably 1 to 6 wt % based on the weight of the composition. Preferably the pH of a 10 wt % solution of the composition in water has a value of 4 to 7, preferably 4.5 to 6.0.

The compositions may contain further additives such as skin moisturizers for example sodium lactate, glycerin, pyrrolidone carboxylic acid; pH-regulans, complexing agents; colorants; whiteners; perfumes; salts such as sodium chloride, sodium sulfate, sodium phosphates; antioxidants, antimicrobial agents and preservatives or stabilizers.

The manufacturing process of the solid surfactant bars is comparable to conventional soap production using fatty acid soaps. The ingredients are mixed and can be processed by kneading, milling, extrusion, cutting and bar pressing into a form suitable for transportation or for application.

Examples

1. Used Raw Materials: alpha-sulfofatty acid disalts (A): Texapon SFA powder (BASF SE): alpha-sulfo fatty acid disalt of technical grade based on native C12/14-fatty acid; composition: 79% by weight disodium 2-sulfolaurate, 8% by weight sodium laurate, 11,8% by weight sodium sulfate, water ad 100% by weight. The term "laurate" here means that the C12/14 weight ratio of the mixture of the underlying native fatty acids is 70:30.

Texapon SFA paste (BASF SE): alpha-sulfo fatty acid disalt of technical grade based on native C12/14-fatty acid; composition: 32.5% by weight disodium 2-sulfolaurate, 4.3% by weight sodium laurate, 4.9% by weight sodium sulfate, water ad 100% by weight. The term "laurate" here means that the C12/14 weight ratio of the mixture of the underlying native fatty acids is 70:30.

Dextrin: from Haiyan Liuhe Pharmaceutical Industry Co. LTD, Sanlian Village, Yucheng Town, Haiyan County. Pharmaceutical Grade Dextrin, mesh size: 120 mesh, reducing sugar <0.20 g. Dehyton PK45 (BASF SE): Dry residue 44 to 46.0 wt %, INCI: Cocamidopropyl Betaine; Eumulgin E033 (BASF SE): Polyethylene glycol 6000 distearate, INCI: PEG-150 Distearate Plantacare 818 UP (BASF SE): C8-C16 fatty alcohol glycoside; INCI: Coco-Glucoside Ucare JR-400 (Dow Chemical): INCI: Polyquaternium-10;

2. Manufacturing of Solid Surfactant Bars

The preparation of the solid surfactant bars comprises the following steps: 1st step: Production of solid surfactant composition in form of noodles:

1. Citric acid was dissolved in demineralized water.
2. Texapon SFA powder and polysaccharide powder were first mixed in a ploughshare mixer (L20, Loedige Process Technology, Gebrüder Lödige Maschinenbau, Paderborn, Germany) at 30 RPM for 3-5 min. Inert gas (e.g. nitrogen gas) was used as protection gas in the mixer to avoid dust explosion.
3. Citric acid solution was then added into the mixer by feeding with a pressure nozzle at 30 RPM for 20-30 min. Then the mixer ran at 50-100 RPM for 20-30 min to form a wet paste. pH of the paste (10 wt % solution in water) after mixing was 5-6.
4. The paste was further mixed in a Mix-Muller (LG, Simpson Technologies, Euskirchen Germany) at 15-30 RPM for 20-30 min and then
5. extruded in an extruder (LSRE 75 R, Sela Maschinen GmbH, Harbke, Germany) with 3 mm dies at 3-10 RPM extrusion speed to produce SFA noodles.

2nd step: Production of bars from solid surfactant noodles:

6. The noodle formed agglomerates were grinded in a three-roller grinding mill (Weber & Seeländer, Harbke, Germany) twice to obtain solid surfactant sheets.
7. The solid surfactant sheets were filled into an extruder machine for soap bars (Weber & Seeländer, Sela-Maschinen GmbH, Harbke, Germany) and pressed to get solid surfactant bars.

3. Anti-Mush Performance Test Method

The soap bar was plunged into a 250 ml beaker, which is filled with 250 ml of demineralized water of 22° C.±2° C. (FIG. 1: apparatus for anti-mush performance test method). The bar was immersed into the water for about 4 cm. The length (a) and width (b) of the bottom surface was measured for calculating the mushy surface (A=a*b).

After 2 hours soaking the bar was removed from the water, carefully shaken to dislodge any surplus of water and weighed (W1).

The mush was then removed by carefully scraping with a plastic scraper the scraped bars were wiped with a tissue and dried overnight before determining the termal weight (W2).

The mush performance was calculated:

$$\text{Mush Percentage \%} = (W2 - W0)/W0$$

W0=Weight of the bar before soaking
W2=Weight of the bar after soaking 2 hr, mush removal and dry overnight For hair care applications one of the key performances is foaming, but mushiness is an additional important property. If the anti-mush value is too low, the bar will be too hard and difficult to be applied on hair. If the anti-mush value is too high, the bar will be too soft and easy to be solved in water. The range for the best mush percentage value of the solid surfactant bars was 5%-40%, preferably 15%-25%.

4. Foaming Test

Brushing Foaming Method

1. Mill the soap bar in the automatic household grinding machine to achieve a particle size of the milled powders from 20 um to 3000 um.
2. Add 0.15g soap powder and 14.85g water in the 50 ml measuring cylinder and shake gently for a homogenous dispersion for 1 min.

Put the tube brush into cylinder and brush vertically for 30 rounds inside the cylinder to create the foam.

3. Remove the brush from the cylinder and read the foam height.

5. Drying Speed Test

Hair Blow Drying Test Protocol

1. Pre-treatment of hair strands Standard hair strands from IHIP, Chinese hair, 15 cm/2 g, bundled and glued in the upper part. Hair strands were cleaned and bleached.
2. Weigh the hair.
3. Rinse hair for 1 minute at a water flow rate of 1L/min, 38° C., comb once with the wide side. Then remove access water with middle and forefinger for 3 times. Weight the wet hair (keep initial water increase 75% of dry hair weight).
4. Lay hair strand on the special tray, treat with certain amount of the product and brush evenly for 30s each side. then incubate, with total time of 3 mins.
5. For wash-off process, rinse hair again for 1 minute at a water flow rate of 1 L/min, 38° C., remove access water with middle and forefinger for 3 times. Weight the wet hair with product (keep initial water increase 75% of dry hair weight). For leave on product, skip step 5, directly go to step 6.
6. Transfer the hair to blow dry setup and blow-dry until <0.05 g increments.
7. Combing hair strand with wide side after 1, 3 and 5 min. of blow drying.
8. Record hair weight every minute.

6. Examples with Solid Surfactant Compositions

In order to compare different fillers for solid soap bars the mush tendency and the foaming properties of the bars have been investigated.

The drying performance after hair cleaning has been tested using these soap bars for shampooing hair.

Stearic acid has been used as comparison to dextrin as a standard filler for solid soap bars.

TABLE 1

Comparison of Solid Surfactant Bar Compositions with Soap Bars Comprising Conventional Soaps (Alkali salts of Fatty Acids) Regarding Foaming Properties, Mushiness and Hair Drying Speed

| Ingredients | | Tradename | Fatty Acid Composition | Inventive S1 | Comp. S2' | Comp. S3' | Comp. S4' |
|---|---|---|---|---|---|---|---|
| Filler | Dextrin | | | 28.6 | | | |
| | Stearic Acid | Edenor ST-05MMY (Oleochemicals) | C16: 60%; C18: 40% | | | | 28.6 |
| | | Wilfarin SA1892 (Wilmar-Intern.) | C16: 8%; C18: 92% | | | 28.6 | |

TABLE 1-continued

Comparison of Solid Surfactant Bar Compositions with Soap Bars Comprising Conventional Soaps (Alkali salts of Fatty Acids) Regarding Foaming Properties, Mushiness and Hair Drying Speed

| Ingredients | Tradename | Fatty Acid Composition | Inventive S1 | Comp. S2' | Comp. S3' | Comp. S4' |
|---|---|---|---|---|---|---|
| | Edenor C18-98MY (Oleochemicals) | C18: 98%; >C18: 2% | | 28.6 | | |
| Texapon SFA powder (A) | | | 52.4 | 52.4 | 52.4 | 52.4 |
| Citric Acid | | | 4.8 | 4.8 | 4.8 | 4.8 |
| Water | | | 14.3 | 14.3 | 14.3 | 14.3 |
| pH (10% solution) | | | 5.04 | 5.49 | 5.43 | 5.41 |
| Foaming Brushing Test (mm) | | | 162 | 95 | 95 | 115 |
| Mushiness (%) | | | 13.9 | 20.4 | 16.1 | 19.1 |
| Time to dry 50 wt % water (min) | | | 3.4 | 4.0 | | |
| Time to dry 80 wt % water (min) | | | 5.6 | 6.7 | | |

TABLE 2

Hair Drying Speed of commercially available bar compositions used as hair cleaning composition.

| | Time to dry 50 wt % water (min) | Time to dry 80 wt % water (min) |
|---|---|---|
| SFA/Dextrin Bar (S1) | 3.4 | 5.6 |
| Water | 3.9 | 5.9 |
| Safeguard Bar | 4.4 | 6.7 |
| Panteen Shampoo | 4.5 | 7 |
| Olay Bar | 4.4 | 7.2 |
| Lush Bar | 4.5 | 7.2 |
| Seeyoung Shampoo | 4.2 | 7.5 |
| Panteen Conditioner | 6 | 10 |

7. Panel Test

Figure 2:
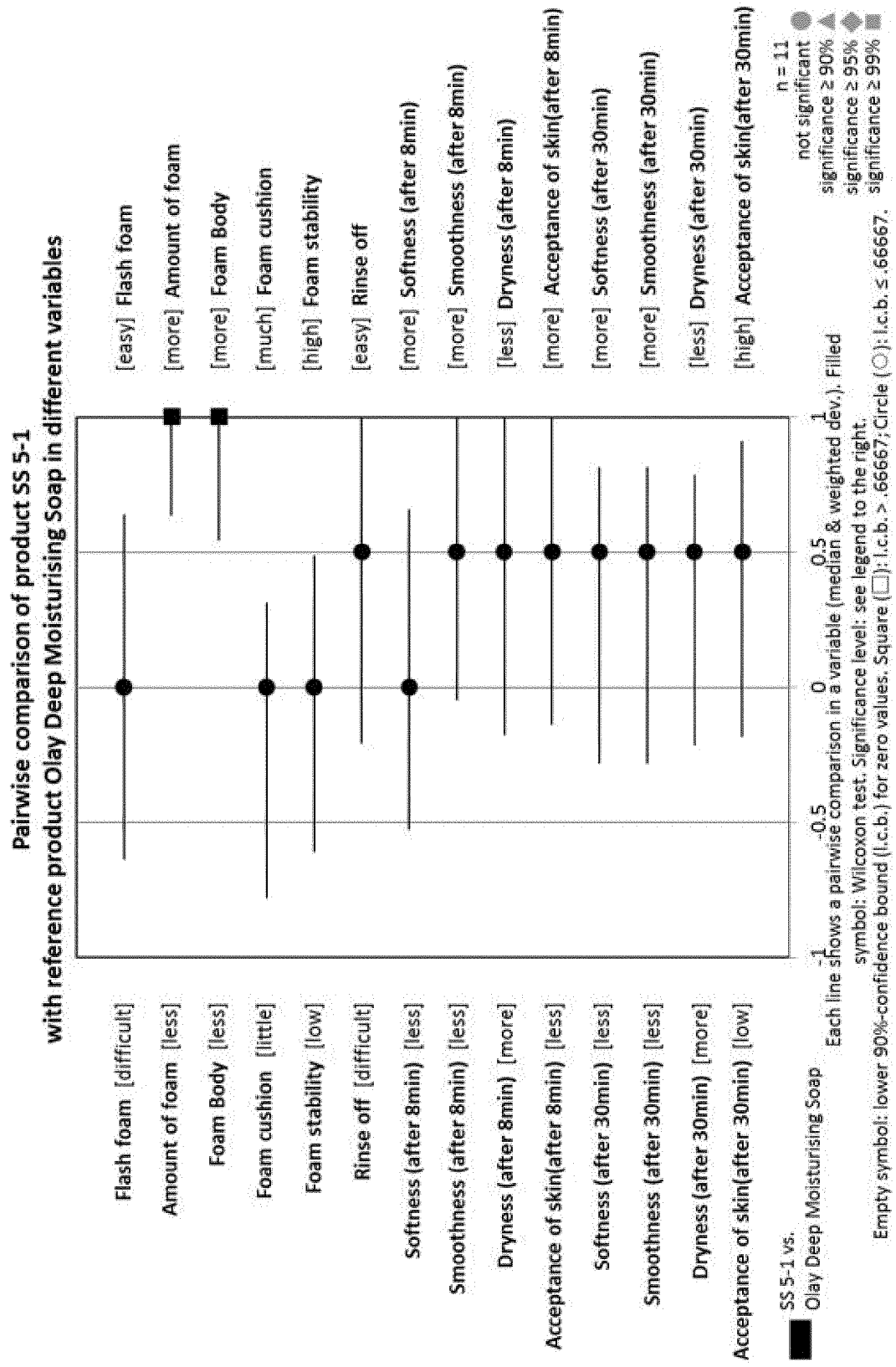

A panel of 11 trained volunteers (9 Chinese females, 2 Chinese males) tested a commercially available solid surfactant bar (Olaz Bar: INCI: Sodium Stearate, Sodium Cocoyl Isethionate, Paraffin, Aqua, Sodium Cocoglyceryl Ether Sulfonate, Glycerin, Sodium Stearate, Talc, Stearic Acid, Sodium Cocoate, Coconut Acid (Coconut Derived), Sodium Isethionate, Sodium Chloride, Titanium Dioxide, Citric Acid, fragrance, PEG-90M) and the solid surfactant composition according to the invention (Sample: S10 of Table 3). One bar of the control product and one bar of the inventive product were used for all eleven panelists. For the foam test, the panelists foamed up the soap bars, described the properties of the foam and then rinsed it off. For the skin test, the panelists rubbed the wetted soap bar onto their forearms for 20 seconds, rinsed and dried them. The tests are performed in an air-conditioned room at a temperature of 22° C. and a relative humidity of 50%. Results are described in FIG. 2 (Results of the Panel Test).

TABLE 3

Comparison of Foaming and Mushiness of Different Solid Surfactant Bar Compositions

| Ingredient | S5' [wt %] | S6 [wt %] | S7 [wt %] | S8 [wt %] | S9 [wt %] | S10 [wt %] | S11 [wt %] | S12 [wt %] | S13 [wt %] | S14 [wt %] | S15 [wt %] |
|---|---|---|---|---|---|---|---|---|---|---|---|
| Stearic Acid (Analytical grade) | 25 | / | / | / | / | / | / | / | / | / | / |
| Dextrin | / | 25 | 35 | 35 | 25 | 30 | / | / | / | 20 | 20 |
| β-Cyclodextrin | / | / | / | / | / | / | 30 | / | / | / | / |
| maltodextrin | / | / | / | / | / | / | / | 30 | / | / | / |
| Potato starch | / | / | / | / | / | / | / | / | 30 | / | / |
| Texapon SFA powder | 50 | 50 | 50 | 50 | 60 | 55 | 55 | 55 | 55 | 55 | 55 |
| Citric Acid | 5 | 5 | 5 | 5 | 5 | 5 | 5 | 5 | 5 | 5 | 5 |
| Plantacare 818 UP | 10 | 10 | / | 5 | / | / | / | / | / | / | / |
| Water | ad 100 | ad 100 | ad 100 | ad 100 | ad 100 | ad 100 | ad 100 | ad 100 | ad 100 | ad 100 | ad 100 |
| Appearance | | | | | | | dry and rough | sticky | poor homogeneity | | |
| pH (10% sol.) | 5.57 | 5.66 | 5.48 | 5.46 | 5.91 | 5.74 | 5.72 | 5.74 | 6.02 | 5.72 | 5.8 |
| Brush Foam (mm) | 80 | 150 | 150 | 148 | 160 | 148 ± 3 | 158 ± 3 | 158 ± 3 | 155 ± 3 | 123 ± 3 | 145 ± 0 |
| Mushiness Percentage | 12.2% | 21.0% | 15.8% | 23.7% | 23.4% | 13.9% | 18.7% | 17.0% | 12.5% | 19.8% | 22.1% |

Examples with Liquid Aqueous Surfactant Compositions

TABLE 4

Comparison of Drying Speed after Treatment with Aqueous Shampoo Compositions

| Part | Ingredients | INCI-Name (AM = active material) | Sample S16 wt % inventive SFA/dextrin | Sample S17', wt % comparative w/o dextrin | Sample S18', wt % comparative with glycerin | Sample S19,'wt % comparative w/o SFA |
|---|---|---|---|---|---|---|
| A | De-ionized Water | Water | ad 100 | ad 100 | ad 100 | ad 100 |
|   | Ucare JR 400 (Dow) | Polyquarternium-10 | 0.3 | 0.3 | 0.3 | 0.3 |
|   | Citric Acid | Citric Acid | 1.3 | 1.3 | 1.3 | 1.3 |
| B | Texapon SFA paste (BASF SE) | Disodium 2-sulfolaurate | 15.3 | 15.3 | 15.3 | / |
|   | Dehyton PK45 (BASF SE) | Cocamidopropyl Betaine | 10.2 | 10.2 | 10.2 | 15.3 |
|   | Plantacare 818 UP (BASF SE) | Coco-Glucoside | 9.2 | 9.2 | 9.2 | 13.8 |
|   | Eumulgin E033 (BASF SE) | PEG-150 Distearate | 1.5 | 1.5 | 1.5 | 1.5 |
| C | Dextrin |  | 3 | / | / | 3 |
|   | Glycerin |  | / | / | 3 | / |
| D | Glydant Liquid plus (DeWolf) | DMDMH (preservative) | 0.5 | 0.5 | 0.5 | 0.5 |
|   | drying time to 50% residual water |  | 3.2 min | 4.4 min | 4.0 min | 4.1 min |

Surprisingly it was found that the addition of dextrin can increase the drying speed of treated hair significantly. (comparison 12 and 16), it is superior to glycerin (comparison 16 and 29).

The invention claimed is:
1. A surfactant composition comprising
one or more alpha-sulfo fatty acid disalt (A) of the general formula (I),

in which the radical $R^1$ is a linear or branched alkyl or alkenyl radical with 6 to 16 carbon atoms and the radicals $M^1$ and $M^2$, independently of one another, are selected from the group consisting of H, Li, Na, K, Ca/2, Mg/2, ammonium, and alkanolamine,
one or more dextrin (B) of the general formula (II),

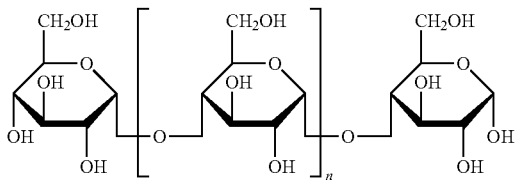

in which n is an integer between 3 and 200, where the following provisos apply:
if the surfactant composition comprises one or more ester sulfonate (E) of the general formula (V),

in which the radical $R^2$ is a linear or branched alkyl or alkenyl radical with 6 to 18 carbon atoms and the radical $R^3$ is a linear or branched alkyl or alkenyl radical with 1 to 20 carbon atoms, where the radical $R^3$ can be an alkenyl radical or be branched only above 3 carbon atoms, and the radical $M^7$ is selected from the group consisting of Li, Na, K, Ca/2, Mg/2, ammonium, and alkanolamine, it is the case that the compound (A), based on the sum of the compounds (A) and (E), must be present to more than 50% by weight;
wherein the surfactant composition is a solid; and
wherein the one or more dextrin (B) is present in an amount of 1 to 6 percent by weight based on the weight of the composition.

2. The surfactant composition according to claim 1 comprising
one or more alpha-sulfo fatty acid disalt (A) of the general formula (I),

in which the radical $R^1$ is a linear or branched alkyl or alkenyl radical with 6 to 16 carbon atoms and the radicals $M^1$ and $M^2$,, independently of one another, are selected from the group consisting of H, Li, Na, K, Ca/2, Mg/2, ammonium, and alkanolamine

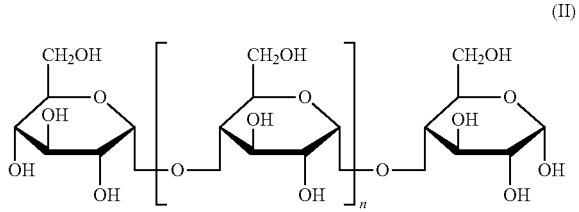

where the following provisos apply:
if the surfactant composition comprises one or more ester sulfonates (E) of the general formula (V),

in which the radical $R^2$ is a linear or branched alkyl or alkenyl radical with 6 to 18 carbon atoms and the radical $R^3$ is a linear or branched alkyl or alkenyl radical with 1 to 20 carbon atoms, where the radical $R^3$ can be an alkenyl radical or be branched only above 3 carbon atoms, and the radical $M^7$ is selected from the group consisting of Li, Na, K, Ca/2, Mg/2, ammonium, and alkanolamine, it is the case that the compound (A), based on the sum of the compounds (A) and (E), must be present to more than 50% by weight.

3. The composition according to claim 1, wherein the compounds compound (A), based on the sum of the compounds (A) and (E), must be present to more than 60% by weight.

4. The composition according to claim 1, wherein the radical R1 in the formula (I) denotes a saturated, linear alkyl radical having 10 to 16 C atoms, with respect to the compound (A) that the proportion of the compounds (A) in which the radical R1 is a decyl or a dodecyl radical, based on the total amount of the compounds (A), is more than 60% by weight.

5. The composition according to claim 1, wherein the radicals M1 and M2 are selected from the group consisting of H (hydrogen) and Na (sodium).

6. The composition according to claim 1 comprising less than 40% by weight anionic surfactants other than compounds (A) and (C) of the general formula (III) based on the weight of the composition, with formula (III) being

  (III), in the formula (III), the radical $R^4$ is a linear or branched alkyl or alkenyl radical with 7 to 19 carbon atoms with respect to the compound (C) that a proportion of the compound (C) in which the radical $R^4$ is an undecyl or a tridecyl radical, based on the total amount of the compound (C), a is more than 60% by weight, and the radical $M^3$ is selected from the group consisting of H, Li, Na, K, Ca/2, Mg/2, ammonium, and alkanolamines.

7. The composition according to claim 1 wherein it is a liquid aqueous composition.

8. The composition according to claim 1, wherein the compound (A) is present in an amount of 0.1 to 10 percent by weight based on the total weight of the composition fora liquid aqueous composition, or the compound (A) is present in an amount of 10 to 90 percent by weight based on the weight of the composition for a solid composition.

9. A for cosmetic product, detergent, or cleaner comprising a composition of claim 1.

10. The cosmetic product according to claim 9 in the form of hair shampoos, solid surfactant compositions, shower gels, soaps, syndets, washing pastes, washing bars, washing lotions, scrub preparations, foam baths, oil baths, shower baths, soap bars, shaving foams, shaving lotions, shaving creams, toothpastes, mouthwashes, lotions, and creams.

* * * * *